US006839406B2

(12) United States Patent
Ries et al.

(10) Patent No.: US 6,839,406 B2
(45) Date of Patent: Jan. 4, 2005

(54) APPARATUS AND METHOD FOR DETECTING ITEMS IN OBJECTS

(75) Inventors: Hermann Ries, Taunusstein (DE); Patricia Schall, Neustadt (DE); Frank Cordes, Neustadt (DE); Martin Hartick, Bad Nauheim (DE)

(73) Assignee: Smiths Heimann GmbH, Wiesbaden (DE)

(*) Notice: Subject to any disclaimer, the term of this patent is extended or adjusted under 35 U.S.C. 154(b) by 0 days.

(21) Appl. No.: 09/860,593

(22) Filed: May 21, 2001

(65) Prior Publication Data

US 2003/0169843 A1 Sep. 11, 2003

Related U.S. Application Data

(63) Continuation of application No. 09/645,484, filed on Aug. 25, 2000, now abandoned.

(30) Foreign Application Priority Data

Nov. 13, 1999 (DE) .......................................... 199 54 662

(51) Int. Cl.[7] ............................................ G01N 23/20
(52) U.S. Cl. ............................ 378/70; 378/88; 378/57
(58) Field of Search ............................ 378/57, 70, 83, 378/88, 147, 71, 82, 86

(56) References Cited

U.S. PATENT DOCUMENTS

| 4,894,855 | A | * | 1/1990 | Kresse ......................... 378/196 |
| 4,956,856 | A | | 9/1990 | Harding |
| 5,182,764 | A | | 1/1993 | Peschmann et al. |
| 5,265,144 | A | * | 11/1993 | Harding et al. ................ 378/86 |
| 5,367,552 | A | * | 11/1994 | Peschmann .................... 378/57 |
| 5,600,303 | A | | 2/1997 | Husseiny et al. |
| 5,642,393 | A | * | 6/1997 | Krug et al. ..................... 378/57 |
| 5,692,029 | A | * | 11/1997 | Husseiny et al. ............... 378/88 |
| 5,712,893 | A | * | 1/1998 | Dykster et al. ................. 378/58 |
| 5,787,145 | A | * | 7/1998 | Geus ............................. 378/71 |
| 6,088,423 | A | * | 7/2000 | Krug et al. ..................... 378/57 |
| 6,122,344 | A | * | 9/2000 | Beevor .......................... 378/88 |
| 6,198,796 | B1 | * | 3/2001 | Yokoyama et al. ............. 378/73 |

FOREIGN PATENT DOCUMENTS

| DE | 41 01 544 A1 | 7/1992 | |
| DE | 41 30 039 A1 | 3/1993 | |
| DE | 44 06 956 C2 | 9/1995 | |
| DE | 195 10 168 A1 | 9/1996 | |
| EP | 0 354 045 A2 | 2/1990 | |
| GB | 1463054 | * 2/1977 | ............ H05G/1/00 |
| GB | 2287163 | * 9/1995 | .......... G01N/23/04 |
| WO | WO 99/66317 | 12/1999 | |

OTHER PUBLICATIONS http://www.heimannsystems.com/newsar.htm, accessed Nov. 6, 2001 (see "Worldwide leadership in X-ray diffraction technology confirmed").

* cited by examiner

Primary Examiner—Craig E. Church
Assistant Examiner—Chih-Cheng Glen Kao
(74) Attorney, Agent, or Firm—Birch, Stewart, Kolasch & Birch, LLP

(57) ABSTRACT

A method and an apparatus for detecting items in objects, such as in luggage, wherein a detector apparatus, functioning as a second detector is divided into a lower testing stage and a higher testing stage. In the lower testing stage, the coordinates of the object location are determined, and subsequently, a diffraction apparatus is moved to this location in the higher testing stage. In particular, X-ray diffraction can be employed to determine the explosive material of the item in the object. The diffraction apparatus comprises a collimator/detector arrangement, which is disposed to be adjusted height-wise and laterally in the higher testing stage, with a laterally-adjustable X-ray source, which is synchronized with the collimator/detector arrangement. The collimator/detector arrangement preferably has only one collimator and one detector. The collimator preferably has a conically-expanding ring slot, which a predetermined angle $\Theta_M$ of a scatter radiation.

23 Claims, 4 Drawing Sheets

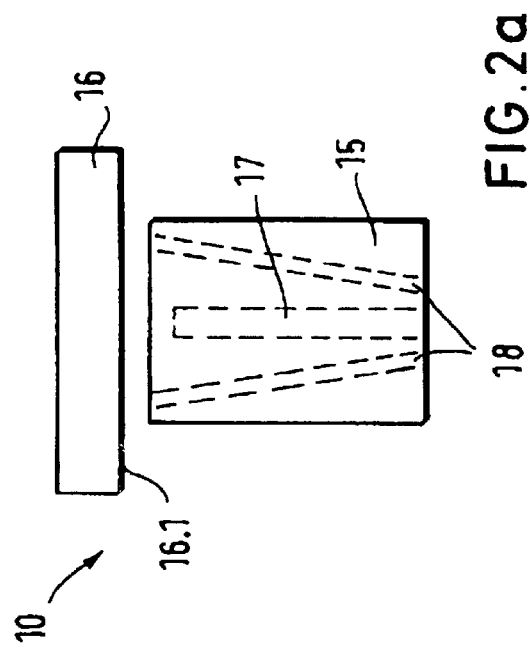
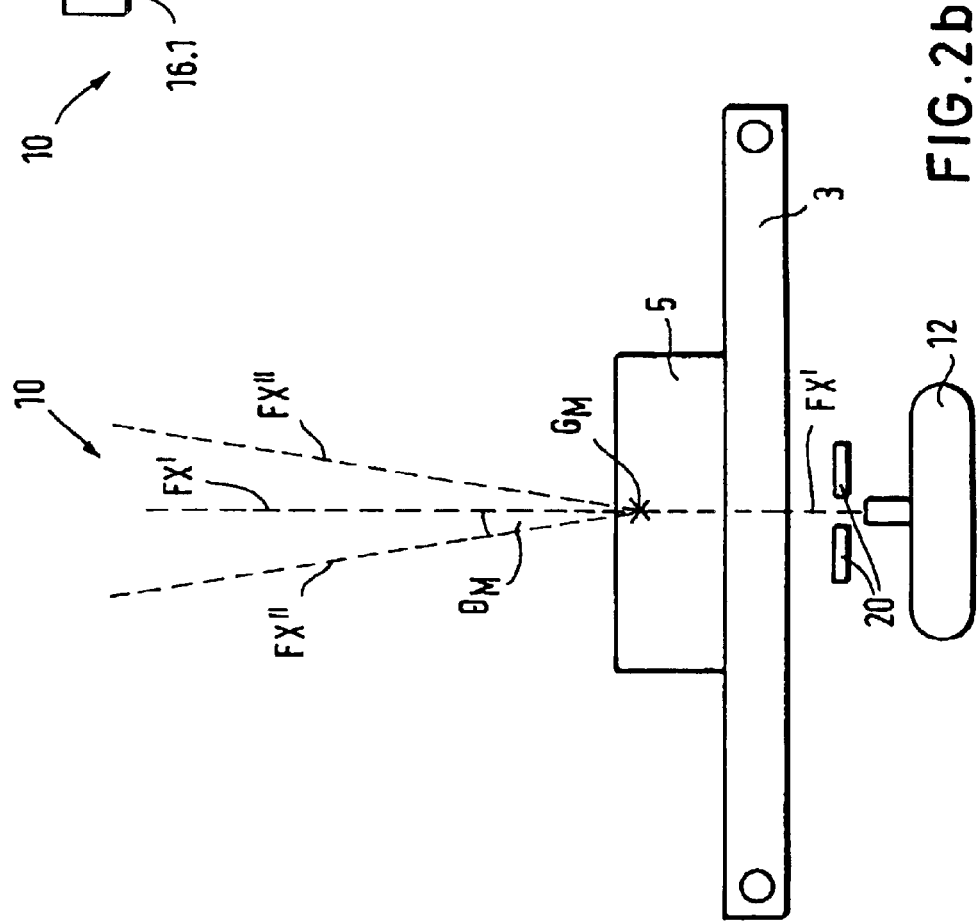

APPARATUS AND METHOD FOR DETECTING ITEMS IN OBJECTS

CROSS-REFERENCE TO RELATED APPLICATION

This application is a continuation of U.S. application No. 09/645,484 filed Aug. 25, 2000 ABN, which is incorporated herein by reference.

This application is related to concurrently filed U.S. Applications Ser. Nos. 09/760,418, 10/080,762 and 09/759,643 and which are continuations of respective U.S. application Ser. Nos. 09/645,485, 09/645,486 and 09/645,487, each filed Aug. 25, 2000, the subject matter of each such application being incorporated herein by reference.

FIELD OF THE INVENTION

The invention relates to an apparatus and a method for detecting items in objects such as luggage.

BACKGROUND OF THE INVENTION

To assure safety in air travel, for example, it is necessary to check luggage for items, particularly explosive agents or materials, by employing the most modern technical equipment. In the process, an object (luggage) typically passes through one or more stages (levels). The first level usually comprises a fast X-ray system designed to handle the large number of luggage items to be tested. If a piece of luggage contains materials that cannot be clearly identified, an additional test is performed in a second level.

As disclosed in German Patent DE 44 06 956 C2, for an accelerated check in the second, or higher, stage, a plurality of coordinates of the regions that were not unambiguously determined in the lower, first stage is detected distinctly by a computer and transmitted to the second or higher stage.

The method of X-ray diffraction can be employed, particularly in the search for explosive materials. In this method, X-ray radiation that has been scattered by the crystal structure of an item is measured and compared to the characteristic energy spectra of, for example, various explosive materials. These spectra give an indication of the presence of an explosive material and additionally information about the explosive material in the object.

German published patent application DE 195 10 168 A1 discloses an apparatus designed for this purpose. In this case, a fanned X-ray beam is generated at the X-ray source by means of a collimator or aperture, and is then radiated onto a test region of a material to be tested. Slot-shaped collimators are disposed symmetrically around the axis of the central X-ray beam, specifically in a plane that extends perpendicular to the fan plane of the X-ray, on the side of the test region opposite the X-ray source. A plurality of detectors performs the evaluation over the entire X-rayed test region.

European published patent application EP 0 354 045 A2 also discloses an apparatus and a method in which a fanned X-ray beam is generated. This fanned beam radiates through the object to be tested, and is diffracted at the lattice structure of the object, with the diffraction being recorded as an energy spectrum by a plurality of detectors. U.S. Pat. No. 4,956,856 discloses a further apparatus. In this case, a narrow X-ray beam(pencil beam) is generated and directed, by means of a rotating roller having a spiral-shaped slot, at an object to be X-rayed. The pencil beam passes through the slot transversely to the object to be tested.

German published patent application DE 41 01 544 A1 discloses the use of a primary beam having a small cross section in an X-ray device. Here, a plurality of detectors and a concentric collimator arrangement detects the scatter radiation generated from the primary beam.

A drawback of the aforementioned apparatuses is that the entire piece of luggage must always be sampled or scanned in order to ascertain all unacceptable luggage items.

An arrangement for generating an expanded X-ray bundle is known from German published patent application DE 41 30 039 A1. A collimator arrangement used for this purpose comprises two limiting bodies, which are oriented relative to one another such that they limit a space corresponding to the shape of the ray bundle. This arrangement serves to increase the surface impacted by the X-ray.

SUMMARY OF THE INVENTION

It is an object of the invention to provide a method for fast, automatic detection of items in objects inside a detection apparatus, and an apparatus for executing the method.

The above object generally is achieved according to a first aspect of the present invention by a method for detecting an item in an object, in which method comprises: in a lower testing stage within a level in a detection apparatus, the object is scanned with x-rays to detect an item, the location of the item is determined in the object, with the location including at least first and second dimensional coordinates of the object, and the location is stored and transmitted to a higher testing stage within the level of the detection apparatus. In the higher testing stage, the unacceptable item is directly tested at the determined location, with the direct testing comprising x-ray diffraction analysis.

The above object additionally achieved according to a second aspect of the invention by an apparatus for detecting an unacceptable item in an object, which apparatus comprises: a detection apparatus having a lower testing stage within a level, a higher testing stage within this level, and a computer, wherein the lower testing stage includes a first X-ray source, a detector device, a transport device for an object disposed between the source and detector device and extending between the lower and higher testing stages, and a marking device, with the detector and marking device being connected to the computer, and wherein the higher testing stage is located downstream from the lower testing stage and comprises a diffraction apparatus, with the diffraction apparatus being adjustably positionable in the higher testing stage and being connected to the computer.

The concept underlying the invention is to split the scanning process, and pre-scan a piece of luggage to be tested in a lower testing stage of the detection apparatus, so that, in a higher testing stage, the luggage item(s) classified as unacceptable in one location/point or a plurality of locations/points ascertained in the lower testing stage and each described by two or three coordinates can be purposefully examined. Thus, in the higher stage, the entire piece of luggage no longer needs to be sampled. This multi-step process saves time and exposes the object to a lower dose of radiation. In the higher testing stage, the previously determined location(s) assists (assist) in the detection of the material type through X-ray diffraction. An airport, for example, thus has at its disposal an effective tool for quickly, simply and automatically testing luggage at the second or higher stage.

This is due to the fact that a point is first determined in the lower testing stage, from a belt or object position and a detector that detects the luggage item, and then is probed by a diffraction apparatus located in the higher testing stage.

The diffraction apparatus preferably comprises a collimator/detector arrangement, which is mounted to be adjusted height-wise and transversely in the higher testing stage, and a conveying element, e.g., a belt, which adjusts or moves the item in the longitudinal direction. The luggage item is scanned at this determined point through X-ray diffraction. To this end, the collimator/detector arrangement and the X-ray source can be adjusted synchronously. Accordingly, the collimator/detector arrangement is preferably mounted to be adjusted in height relative to the X-ray source.

If two coordinates are known, the diffraction apparatus can be used to scan the luggage item for the third coordinate, or, if the three coordinates are known, the item is only measured at this point. Thus, the diffraction apparatus is set either to the belt position determined as the X coordinate, and adjusted vertically and laterally in the beam path, or it is set directly into this point.

The height-adjusted collimator/detector arrangement preferably comprises an adjustable round-slot collimator in the form of a truncated cone with a detector located behind it.

In addition, the exact spatial position and dimensions of the unacceptable item in the luggage can be determined, namely in its X, Y and Z coordinates, in the higher testing stage.

In a further step, additional information can be obtained for identifying the material. For this purpose, the round-slot collimator has a central, blind-bore-like opening, in which two different, spatially-separate detector devices are disposed one behind the other, the devices being used in a known manner to determine the average atomic number of the item located in the primary beam.

The lower and higher testing stages are preferably located in a common detection apparatus of the second (higher) level.

The invention is described in detail by way of a preferred embodiment, with reference to the drawing.

BRIEF DESCRIPTION OF THE DRAWINGS

FIG. 2a illustrates a preferred collimator/detector arrangement for the apparatus of FIG. 2.

FIG. 2b illustrates the functioning principle of the detection apparatus of FIG. 2.

DETAILED DESCRIPTION OF THE PREFERRED EMBODIMENTS

In a first (or lower) detection level of a detection arrangement, not shown in detail, a piece of luggage 5 (object) is tested for security-relevant material that the object 5 may contain. If a suspicious object is detected, this object 5 enters a second (or higher) detection level for further testing and assessment of the material of suspicious luggage items (items) 6 and/or 7. These levels are known to be spatially separated from one another.

In the illustrated example, this second level, in which the material is determined, is the primary focus.

Preferably, two testing stages 30.1 and 30.2 are located inside the detection apparatus 30, with 30.1 being the lower testing stage and 30.2 being the higher testing stage.

Figure 1:
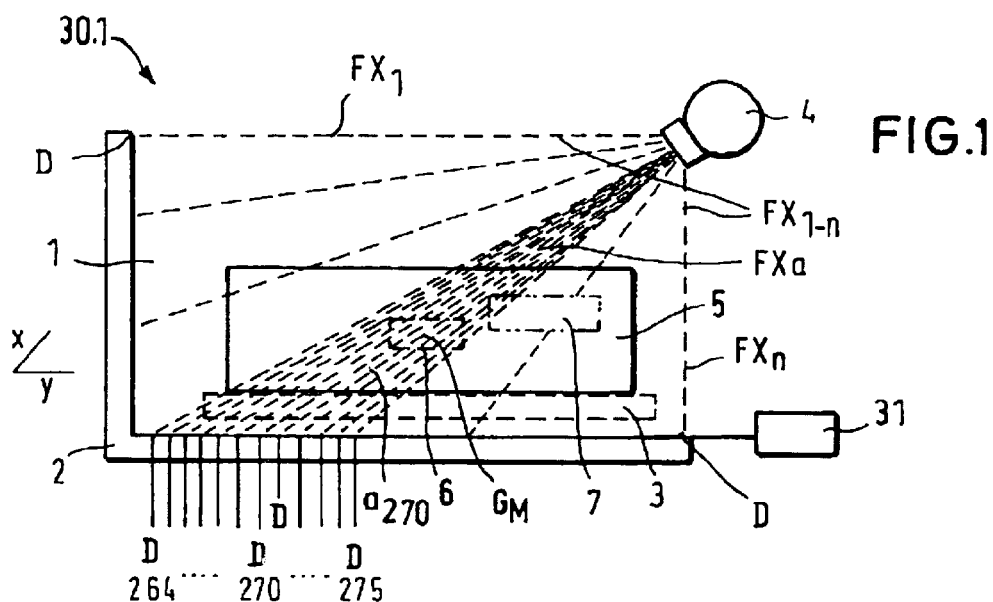
FIG. 1 is a simplified representation of the X-raying of an object with items in an X-ray tunnel of a lower testing stage of a detection apparatus.

FIG. 1 depicts the lower testing stage 30.1.

The object 5 is brought into a known X-ray tunnel 1 of the lower testing stage 30.1 of the detection apparatus 30, not shown in detail. Disposed in the X-ray tunnel 1 are, for example, an L-shaped X-ray detector apparatus 2, a transport device 3 used also as the reference plane of the horizontal plane and, to the side, an X-ray source 4. The X-ray source 4 is preferably located above the transport device 3 and opposite the detector apparatus 2. The object 5 with the items 6, 7 to be X-rayed is located on the transport device 3.

The detector apparatus 2 comprises a plurality of individual detectors $D_{1-n}$, with which the type of material is detected in a conventional manner. For the sake of a clear overview, the detectors $D_{1-n}$ are only illustrated over a small region of detector apparatus 2. For material detection, the X-ray source 4 preferably generates a fanned X-ray beam FX composed of rays FX, to $FX_n$ in a known manner. The fanned beam passes through the X-ray tunnel 1 and the object 5, preferably with a narrow cross section. The L shape of the detector apparatus 2 and the individual arrangement and orientation of the individual detectors $D_{1-n}$ ensure that the X-rays $FX_{1-n}$ of the X-ray fan impact each detector $D_{1-n}$ at a right angle. A plurality of X-ray fans of various energies and/or directions can also be used in other embodiments.

If one or more items 6, 7 is or are located in the respective beam path $a_{1-n}$, of the X-rays $FX_{1-n}$, these X-rays $FX_{1-n}$ are attenuated due to their interaction with the item. The resultant attenuation is detected by the detectors $D_{1-n}$ lying respectively, in the beam paths $a_{1-n}$.

Figure 2:
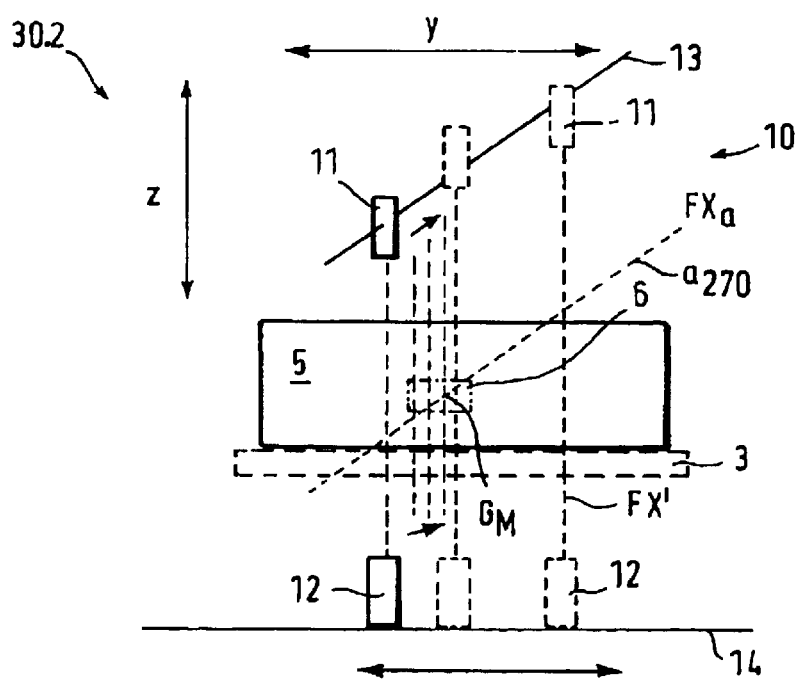
FIG. 2 is a schematic representation of the apparatus of the invention, in a higher testing stage.

FIG. 2 schematically illustrates the higher testing stage 30.2. Here, the object 5 on the transport device 3 is preferably transported from the lower testing stage 30.1 into the higher testing stage 30.2 of the detection apparatus 30, which has an adjustable diffraction apparatus 10. This diffraction apparatus comprises a collimator/detector arrangement 11 and an X-ray source 12. The collimator/detector arrangement 11 is oriented toward an X-ray beam FX', preferably a primary beam of the X-ray source 12 in the form of a 'pencil beam' where the X-ray source is preferably disposed beneath the transport device 3. The collimator/detector arrangement 11 is mounted to be simultaneously adjusted in vertical and lateral positions(in the Z and Y directions, respectively) by element 13, not shown in detail here. Parallel thereto, the X-ray source 12 is secured to elements 14, and can likewise be adjusted laterally in the Y direction. The collimator/detector arrangement 11 and the X-ray source 12 are guided synchronously, with the elements 13 and 14, for example, linear guidance with a spindle drive, being centrally actuated. This can be coordinated by a computer 31, not shown in detail here. FIG. 2a shows a preferred embodiment of the collimator/detector arrangement 11 from FIG. 2 for X-ray diffraction.

The collimator 15 comprises a round slot 18 in the form of a truncated cone such that, of the scatter radiation originating from the tested point of the object, only the components that fall within a specific angle $\Theta_M$ are allowed through. An X-ray-sensitive surface 16.1 of a detector 16 located behind the collimator captures this scatter radiation. If the collimator/detector arrangement 11 is intended to perform additional functions (to be explained below), the collimator 15 has a central, blind-bore-like opening 17.

FIG. 2b is a simplified representation of the functioning principle of the X-ray diffraction. To attain a primary beam FX', a collimator arrangement 20, such as an apertured-diaphragm arrangement, is mounted in front of the X-ray source 12. The transport device 3, with the object 5 on it, is located above the X-ray source 12. When the primary beam FX' impacts a material, the beam is known to be partially deflected as scatter radiation FX" at the crystal-lattice structure of the material (Bragg's Law). Accordingly, the crystal structure, and thus the material, can be determined from the energy spectrum obtained with the energy-sensitive detector 16. In particular, explosive materials can be recognized and distinguished based on their known spectra.

Figure 3:
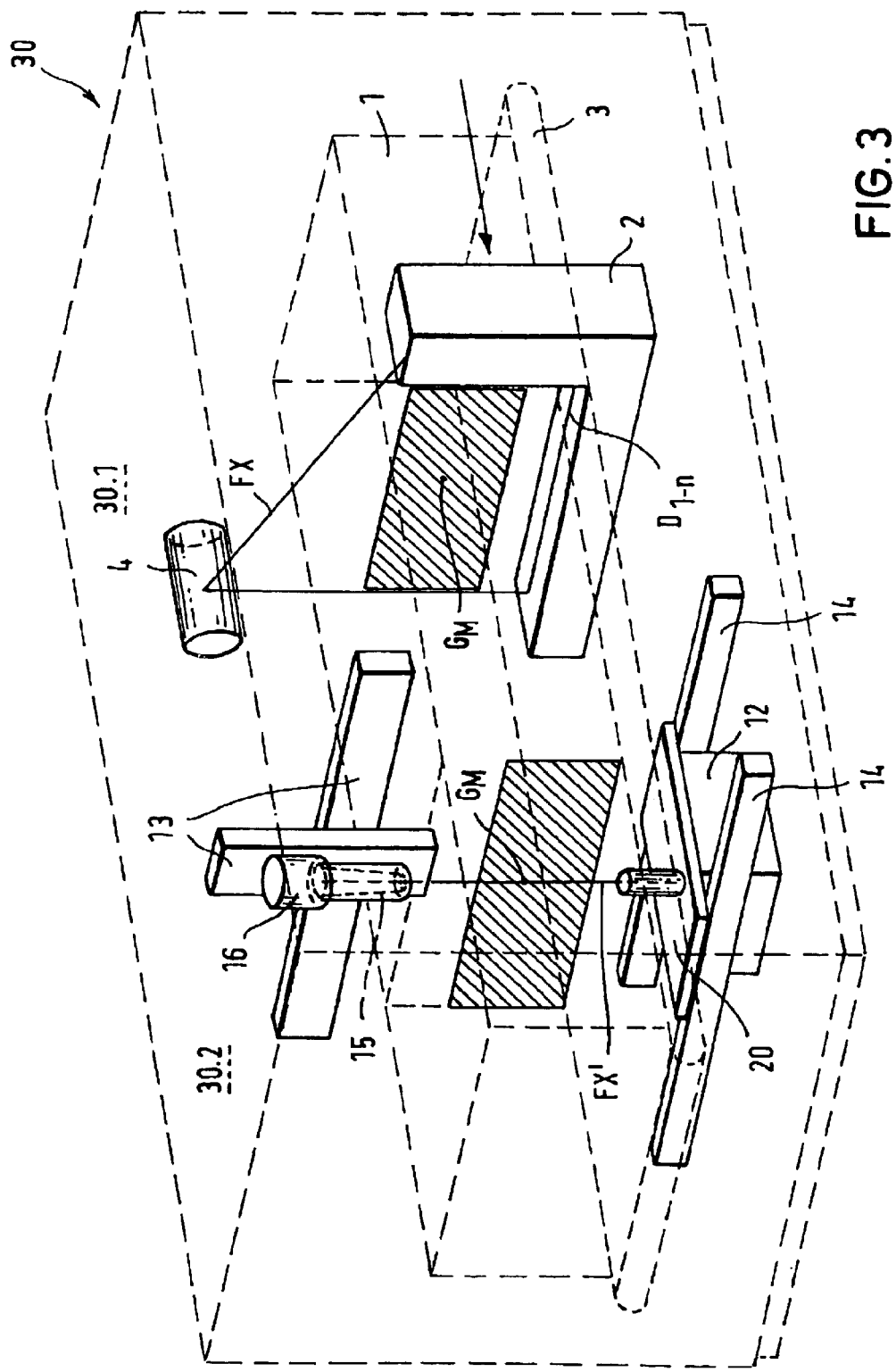
FIG. 3 is a perspective representation of the detection apparatus comprising the parts shown in FIGS. 1 and 2.

For the sake of a better overview, the most crucial details from FIGS. 1 and 2 are combined in a perspective view of the detection apparatus 30 in FIG. 3, where the elements 13 and 14 are shown more clearly.

In the example, only the detection of the item 6 is shown in detail in the various views of FIGS. 1 through 3 in order to present a clear overview.

As the object 5 enters the lower testing stage 30.1, a marking device, not shown in detail here, reads a first belt or position mark $X_1$ into a memory of a computer 31; the mark characterizes the beginning of the object 5. The marking device can be, for example, a light barrier. As the object 5 is transported further, additional belt positions are written into the memory, for example through pixel counting. In the detection of the item 6, a so-called initial belt position $X_{AG}$ is enter ed into the memory. In addition to the determined belt positions, the signals of the detectors $D_{266-275}$, which record the attenuation, and the associated beam paths $a_{1-n}$, are read into the memory, or a further memory, of the computer 31.

From these stored data, a location $G_M$ of the item 6 is determined in the image processing according to special criteria. This location can be described, for example, by two coordinates, with the X coordinate being determined from the initial belt position $X_{AG}$ and the Y coordinate being determined from the detecting detector $D_{270}=G_{AA}$. The beam path $a_{270}$ associated with this detector $D_{270}$ is likewise stored. In the description of a location point $G_M$ in three spatial coordinates, for example, with the use of an additional radiation direction and an additional detector arrangement in the lower testing stage 30.1, the center point of the X-rayed surface of the item 6 located in the beam path $FX_{1-n}$, which results from $X_{GM}$, $Y_{GM}$ and $Z_{GM}$, is determined. This is also read into the memory of the computer 31, and the result is stored there.

The computer 31 transmits these data to the higher testing stage 30.2 of the detection apparatus 30.

In the higher testing stage, the diffraction apparatus 10 is now moved to the coordinates of the location or location point $G_M$, which were transmitted from the lower testing stage 30.1 to the higher testing stage 30.2.

If two coordinates of the location $G_M$ are known, the diffraction apparatus 10 is preferably moved into the initial belt position $X_{AG}$ determined for the item 6. The collimation/detector apparatus 12 is subsequently moved parallel to the direction $a_{270}$, that is, synchronously in the vertical and lateral directions, with the scatter radiation that was generated in the item along the line $a_{270}$ being detected in an energy-selective manner. The X-ray source is accordingly moved synchronously in the lateral direction.

The energy-sensitive signals are stored in one or more temporally-sequential energy spectra, which also permits a spatial distinction among the measured materials along the line $a_{270}$.

In the computer 31, these spectra are compared with known energy spectra in a known manner. This comparison serves to identify the material, particularly an explosive material.

If the location point $G_M$ determined by the lower testing stage is known in three spatial coordinates, the item 6 is conveyed into the predetermined belt position $X_{GM}$, and the collimator/detector arrangement 11 and the X-ray source 12 of the diffraction apparatus 10 are brought into the location point $G_M$ such that, in this point $G_M$, the scatter radiation point FX" of the X-ray source 12, which is deflected at the crystal lattice of the item 6, is captured through the round slot 18 of the collimator 13. In this case, it is not necessary to perform an additional adjustment for determining the type of material.

It is also possible to combine the coordinate information from the lower testing stage and the additional spatial information from the higher stage, possibly expanded by numerous measuring sweeps, and thus determine the volume and the precise spatial position of the item 6 in the object 5.

Figure 4:
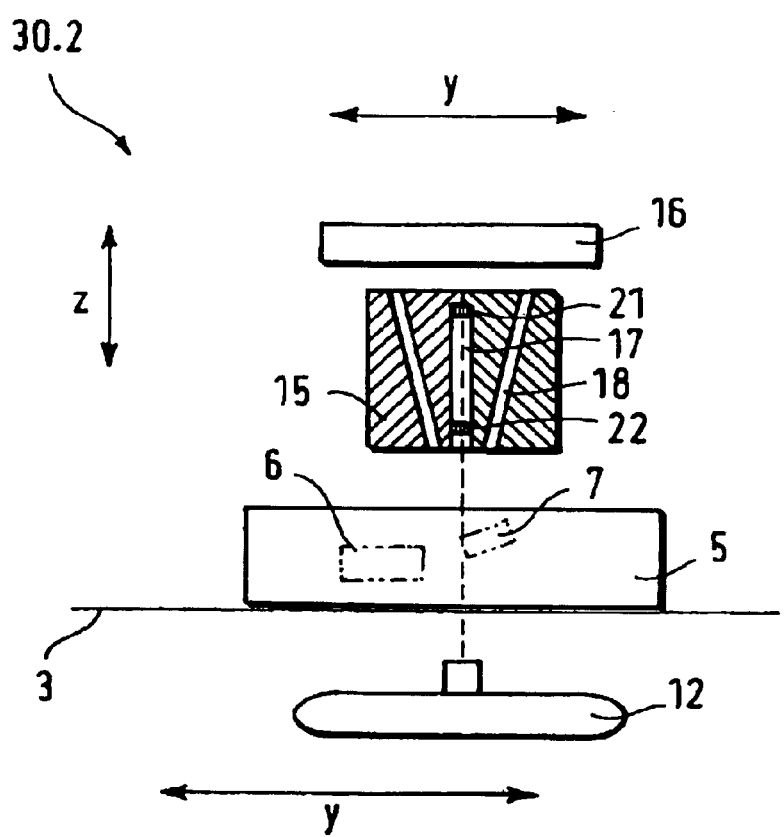
FIG. 4 is a further representation of the collimator/detector arrangement from FIG. 2.

FIG. 4 illustrates an advantageous embodiment of the round-slot collimator 15. A central, blind-bore-like opening 17 is preferably integrated into the collimator 15. Disposed in the opening 17 are a first detection device 22 and, behind it at a defined distance, a second detection device 21. The first detection device 22 is embodied as a detector for relatively lower X-ray energies, and the second detection device 21 is embodied as a detector for relatively higher X-ray energies. The collimator 15 can additionally be used, for example, to perform a conventional material detection through the determination of the average atomic number of the material of the item 6. The combination of this average atomic number and the determined energy spectrum can provide an improved identification of the material of the item 6. This is of particular significance if the item 6 contains a highly-absorbent material. Often, lower energies of the central beam FX' are absorbed in the material, so the corresponding lines of diffraction are missing in the measured energy spectrum. This absence can be reported to the computer 31 with the additional determination of material, and considered in the comparison for the evaluation.

These detection devices 22, 21 can also perform a precise spatial orientation (adjustment) of the collimation/detection arrangement 11 relative to the X-ray source 12. The adjustment itself is effected without an object 5 being located between the collimation/detection arrangement 11 and the X-ray source 12.

Of course, modifications are possible within the scope of the concept of the invention.

For example, the testing stages 30.1 and 30.2 can be separate, so the describing coordinates can be determined in the lower testing stage as the first stage, then transmitted to the higher—here, the second—stage; it must be ensured that the correct position of the coordinates determined in the first stage is transmitted to the second stage.

Other diffraction apparatuses 10 can also be used, such as those described in the state of the technology, in which case the diffraction apparatus 10 must be adjustable, as disclosed in the description.

The invention now being fully described, it will be apparent to one of ordinary skill in the art that many changes and modifications can be made thereto without departing from the spirit or scope of the invention as set forth herein.

What is claimed is:

1. A method for detecting an item in an object, comprising the steps of:

in a lower testing stage in a detection apparatus,
scanning the object with x-rays to detect said item;
determining the location of said item in said object, said location including only one set of first and second dimensional coordinates of said item, said location being representative of a point within said object; and transmitting said location to a higher testing stage in said detection apparatus; and in said higher testing stage, directly testing said item at said location, with said direct testing comprising x-ray diffraction analysis, said diffraction apparatus comprising an x-ray source and a detector, the x-ray source being adjustably positioned in a plane parallel to a travel direction of said object, the detector being adjustably positioned in a plane parallel and in a plane perpendicular to the travel direction of said object, wherein the x-ray source and detector are positioned separately and synchronously on the basis of said point.

2. The method of claim 1, wherein said first dimensional coordinate of said location is determined from a detector associated with a beam path of a fanned x-ray beam, and said second dimensional coordinate is determined from an initial belt position of the item on a transport device for transporting the object between the two testing stages.

3. The method of claim 1, wherein a spatial position and dimension of said item in said object is determined in said higher testing stage.

4. The method of claim 1, wherein said object is luggage.

5. The method of claim 1, wherein in said higher testing stage said item is directly tested at said location by positioning the diffraction apparatus at said location.

6. The method according to claim 1, wherein said item is directly tested at said location in said higher testing stage with a pencil shaped X-ray beam.

7. A method for detecting an item in an object, comprising the steps of:

in a lower testing stage in a detection apparatus, scanning the object with x-rays to detect said item;

determining the location of said item in said object, said location including only one set of first, second, and third dimensional coordinates of said item, said location being representative of a point within said object; and transmitting said location to a higher testing stage in said detection apparatus; and in said higher testing stage, directly testing said item at said location, with said direct testing comprising x-ray diffraction analysis with a diffraction apparatus, said diffraction apparatus comprising an x-ray source and a detector, the x-ray source being adjustably positioned in a plane parallel to a travel direction of said object, the detector being adjustably positioned in a plane parallel and in a plane perpendicular to the travel direction of said object, wherein the x-ray source and detector are positioned separately and synchronously on the basis of said point, and wherein said third dimensional coordinate is determined from a fanned X-ray beam in said lower testing stage.

8. The method of claim 7, wherein said step of directly testing includes moving the diffraction apparatus in said higher testing stage directly to interrogate the location described by said first, second, and third dimensional coordinates, and converting scattered radiation resultant from this location into a signal that can be evaluated and subjected to processing.

9. The method of claim 7, wherein a spatial position and dimension of said item in said object is determined in said higher testing stage.

10. The method of claim 7, wherein said object is luggage.

11. A method for detecting an item in an object, comprising the steps of:

in a lower testing stage in a detection apparatus, scanning the object with x-rays to detect said item;

determining the location of said item in said object, said location including only one set of first and second dimensional coordinates of said item, said location being representative of a point within said object; and transmitting said location to a higher testing stage in said detection apparatus; and in said higher testing stage, directly testing said item at said location, with said direct testing comprising x-ray diffraction analysis with a diffraction apparatus, said diffraction apparatus comprising an x-ray source and a detector, the x-ray source being adjustably positioned in a plane parallel to a travel direction of said object, the detector being adjustably positioned in a plane parallel and/or in a plane perpendicular to the travel direction of said object, wherein the x-ray source and detector are positioned synchronously on the basis of said point, wherein said first dimensional coordinate of said location is determined from a detector associated with a beam path of a fanned x-ray beam, wherein said second dimensional coordinate is determined from an initial belt position of the item on a transport device for transporting the object between the two testing stages, and wherein said step of directly testing includes moving the diffraction apparatus in said higher testing stage directly to interrogate the location of said item, with said diffraction apparatus being further moved at least one of vertically and laterally along the beam path determined in said lower testing stage, and converting scattered radiation resultant from the detection of the item in the higher testing stage into a signal that can be evaluated and subjected to processing.

12. A method for detecting an item in an object, comprising the steps of:

in a lower testing stage in a detection apparatus, scanning the object with x-rays to detect said item;

determining the location of said item in said object, said location including only one set of first and second dimensional coordinates of said item, said location being representative of a point within said object; and transmitting said location to a higher testing stage in said detection apparatus;

in said higher testing stage, directly testing said item at said location, with said direct testing comprising x-ray diffraction analysis with a diffraction apparatus; and determining an average atomic number of the material of said item, said determining comprising using first and second detection devices disposed inside said diffraction apparatus, wherein said first dimensional coordinate of said location is determined from a detector associated with a beam path of a fanned x-ray beam, and said second dimensional coordinate is determined from an initial belt position of the item on a transport device for transporting the object between the two testing stages, and
wherein said step of directly testing includes moving the diffraction apparatus in said higher testing stage directly to interrogate the location of said item, with said diffraction apparatus being further moved at least one of vertically and laterally along the beam path determined in said lower testing stage, and converting scattered radiation resultant from the detection of the item in the higher testing stage into a signal that can be evaluated and subjected to processing.

13. A method for detecting an item in an object, comprising the steps of:
in a lower testing stage in a detection apparatus,
scanning the object with x-rays to detect said item;
determining the location of said item in said object, said location including only one set of first, second, and third dimensional coordinates of said item, said location being representative of a point within said object; and
transmitting said location to a higher testing stage in said detection apparatus; and
in said higher testing stage,
directly testing said item at said location, with said direct testing comprising x-ray diffraction analysis with a diffraction apparatus, and
determining an average atomic number of the material of said item, said determining comprising using first and second detection devices disposed inside said diffraction apparatus,
wherein said third dimensional coordinate is determined from a second fanned X-ray beam in said lower testing stage, and
wherein said step of directly testing includes moving the diffraction apparatus in said higher testing stage directly to interrogate the location described by said first, second, and third dimensional coordinates, and converting scattered radiation resultant from this location into a signal that can be evaluated and subjected to processing.

14. An apparatus for detecting an item in an object, comprising:
a detection apparatus having a lower testing stage, a higher testing stage, and a computer;
said lower testing stage comprising a first X-ray source, a detector device, a transport device for an object disposed between the source and detector device, and a marking device for indicating a position of an object on the transport device, with said detector device and said marking device being connected to said computer,
said higher testing stage being located downstream from said lower testing stage and comprising a diffraction apparatus, with said diffraction apparatus being adjustably positionable in said higher testing stage and being controlled by said computer,
wherein said diffraction apparatus is positioned based on a location, which is representative of a point within said object, said diffraction apparatus comprising a second x-ray source and a detector, the second x-ray source being adjustably positioned in a plane parallel to a travel direction of said object, the detector being adjustably positioned in a plane parallel and in a plane perpendicular to the travel direction of said object, and
wherein the second x-ray source and detector are positioned separately and synchronously on the basis of said point.

15. The apparatus of claim 14, wherein
said detector of said diffraction apparatus is a collimator/detector apparatus,
said second X-ray source being adjustable laterally by a first adjustment element controlled by the computer;
said collimator/detector apparatus is oriented toward said second X-ray source; and
said collimator/detector is mounted on a second adjustment element controlled by the computer to adjust the height of said collimator/detector relative to said second X-ray source, and to adjust the collimator/detector laterally and synchronously with lateral adjustments of said second X-ray source.

16. The apparatus of claim 15, wherein said collimator/detector arrangement comprises a collimator and a detector having an X-ray sensitive surface disposed behind said collimator, said collimator defining a conically-expanding round slot, which simulates a predetermined angle, said round slot being oriented toward the X-ray sensitive surface of said detector.

17. The apparatus of claim 14, wherein said detector of said diffraction apparatus is a collimator/detector apparatus, and said diffraction apparatus further comprises:
a first adjustment element for laterally adjusting said second X-ray source, said first adjustment element being controlled by said computer;
a second adjustment element for laterally and vertically adjusting said collimator/detector, said second adjustment element being controlled by said computer,
whereby a spacing between said collimator/detector and said second X-ray source is adjustable, and the collimator/detector is laterally adjustable synchronously with lateral adjustments of said second X-ray source.

18. An apparatus for detecting an item in an object, comprising:
a detection apparatus having a lower testing stage, a higher testing stage, and a computer;
said lower testing stage comprising a first X-ray source, a detector device, a transport device for an object disposed between the source and detector device, and a marking device for indicating a position of an object on the transport device, with said detector device and said marking device being connected to said computer; and
said higher testing stage being located downstream from said lower testing stage and comprising a diffraction apparatus, with said diffraction apparatus being adjustably positionable in said higher testing stage and being controlled by said computer,
wherein said diffraction apparatus is positioned based on a location, which is representative of a point within said object,
wherein said diffraction apparatus comprises a second X-ray source and a collimator/detector apparatus, said second X-ray source being adjustable laterally by a first adjustment element controlled by the computer,
wherein said collimator/detector apparatus is oriented toward said second X-ray source, and said collimator/detector is mounted on a second adjustment element controlled by the computer to adjust the height of said collimator/detector relative to said second X-ray source, and to adjust the collimator/detector laterally synchronously with lateral adjustments of said second X-ray source,
wherein said collimator/detector arrangement comprises a collimator and a detector having an X-ray sensitive surface disposed behind said collimator, said collimator defining a conically-expanding round slot, which simulates a predetermined angle, said round slot being oriented toward the X-ray sensitive surface of said detector, and wherein said collimator additionally has a central blind-bore opening containing first and second exactly spaced detection devices.

19. The apparatus of claim 18, wherein said first and second detection devices detect relatively lower and higher energy X-rays, respectively.

20. The apparatus of claim 18, wherein the collimator/detector arrangement is oriented toward a primary beam of the second X-ray source and aligned thereto using the first and second detection devices.

21. An X-ray examining apparatus for detecting an item in an object, comprising:

a transport device for transporting the object through the X-ray examining apparatus;

a lower testing stage having a first X-ray source for producing a fan shaped X-ray beam and a L-shaped detector, the object being transported by the transport device through the fan shaped X-ray beam; and a higher testing stage being located downstream from the lower testing stage, the higher testing stage including a second X-ray source, a second detector, and a collimator, the collimator allowing an X-ray beam to pass therethrough from the second X-ray source to the second detector, wherein upon detection of an item in the object in the lower testing stage, the lower testing stage provides the higher testing stage with a point location of the item within the object, wherein the second X-ray source, the second detector, and the collimator are synchronously and adjustably positioned based upon the point location of the item within the object, wherein the second x-ray source is adjustably positioned in a plane parallel to a travel direction of said object, the detector and collimator are adjustably positioned in a plane parallel and in a plane perpendicular to the travel direction of said object, and wherein the second X-ray source and the second detector are adjustable separately from one another.

22. A method for detecting an item in an object, comprising the steps of:

transporting an object through an X-ray examining apparatus;

detecting, in a lower testing stage, the item in the object, the lower testing stage utilizing at least a first X-ray source, which produces a fan shaped X-ray beam, and a L-shaped detector for detecting the item;

determining a point location of the detected item in the object;

providing a higher testing stage with the point location of the detected item, the higher testing stage having a second X-ray source, a second detector, and a collimator;

adjusting a position of the second X-ray source and the second detector separately and synchronously based upon the point location of the item within the object, the second x-ray source being adjustably positioned in a plane parallel to a travel direction of said object, the detector and collimator being adjustably positioned in a plane parallel and in a plane perpendicular to the travel direction of said object; and examining, in the higher testing stage via the second X-ray source, the second detector, and the collimator, the object at the point location of the item within the object.

23. An X-ray examining apparatus comprising:

a lower testing stage having a first x-ray source and a first detector associated therewith, the lower testing stage scanning an object with x-rays and determining a location of an item within the object; and a higher testing stage being provided downstream from the lower testing stage and receiving the object from the lower testing stage via a transport device, the higher testing stage having a second x-ray source and a second detector, the second x-ray source and second detector being adjustably and separately positioned from one another in a plane parallel or in a plane perpendicular to a travel direction of the object on the basis of the location of the item within the object, the higher testing stage directly examining the item within the object via x-ray diffraction analysis.

* * * * *

UNITED STATES PATENT AND TRADEMARK OFFICE
CERTIFICATE OF CORRECTION

PATENT NO. : 6,839,406 B2
DATED : January 4, 2005
INVENTOR(S) : Ries et al.

It is certified that error appears in the above-identified patent and that said Letters Patent is hereby corrected as shown below:

Title page,
Item [75], Inventors, please change;
"[75] Inventors: Hermann Ries, Taunusstein (DE);
    Patricia Schall, Neustadt (DE);
    Frank Cordes, Neustadt (DE);
    Martin Hartick, Bad Nauheim (DE)"

to:

-- [75] Inventors: Hermann Ries, Taunusstein (DE);
    Patricia Schall, Neustadt (DE);
    Frank Cordes, Neustadt (DE);
    Martin Hartick, Bad Nauheim (DE);
    Georg Geus, Wiesbaden (DE) --

Signed and Sealed this

Twenty-fourth Day of May, 2005

JON W. DUDAS
*Director of the United States Patent and Trademark Office*